(12) United States Patent
Weathers et al.

(10) Patent No.: US 8,114,664 B2
(45) Date of Patent: Feb. 14, 2012

(54) SCALABLE WALL BIOREACTOR FOR CULTURE OF PLANT AND ANIMAL TISSUES

(75) Inventors: Pamela J. Weathers, Stow, MA (US); Melissa J. Towler, Worcester, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 636 days.

(21) Appl. No.: 12/172,781

(22) Filed: Jul. 14, 2008

(65) Prior Publication Data

US 2009/0017529 A1 Jan. 15, 2009

Related U.S. Application Data

(60) Provisional application No. 60/949,280, filed on Jul. 12, 2007.

(51) Int. Cl.
*C12M 1/00* (2006.01)
*C12M 3/00* (2006.01)
*C12N 5/00* (2006.01)

(52) U.S. Cl. ............... 435/294.1; 435/298.1; 435/289.1; 435/293.1; 435/303.1; 435/420; 435/430

(58) Field of Classification Search ............... 435/294.1, 435/298.1, 289.1, 293.1, 303.1, 420, 430
See application file for complete search history.

(56) References Cited

U.S. PATENT DOCUMENTS

| 4,291,499 A | * | 9/1981 | Prewer ......................... 47/59 R |
| 4,857,464 A | | 8/1989 | Weathers et al. |
| 5,017,490 A | * | 5/1991 | Taiariol et al. ................ 435/401 |
| 2009/0023194 A1 | * | 1/2009 | Schmidt et al. ............ 435/173.1 |

FOREIGN PATENT DOCUMENTS

WO WO-2007068467 A1 * 6/2007

OTHER PUBLICATIONS

ROOTec bioactives GmbH, "Hair roots as an alternative to molecular farming in the fields," www.rootec.com, dated Dec. 6, 2005.
ROOTec bioactives, Ltd., "Process," High-quality plant-derived compounds, www.rootec.com, downloaded Aug. 8, 2011.

* cited by examiner

*Primary Examiner* — Nathan Bowers
(74) *Attorney, Agent, or Firm* — Burns & Levinson, LLP; Jacob N. Erlich, Esq.

(57) ABSTRACT

A flexible wall bioreactor is described that uses a small droplet size mist unit, a lower rate ambient air flow rate, and a flexible wall culture chamber to provide an environment that allows for the growth of dense root matrix, shoot cultures, and 2 and 3 dimensional animal tissues.

17 Claims, 8 Drawing Sheets

FIG. 5b  μ (DAY$^{-1}$)

FIG. 6b

SCALABLE WALL BIOREACTOR FOR CULTURE OF PLANT AND ANIMAL TISSUES

CROSS REFERENCE TO RELATED APPLICATIONS

This application claims priority to a U.S. provisional application Ser. No. 60/949,280 entitled SCALABLE WALL BIOREACTOR FOR CULTURE OF PLANT AND ANIMAL TISSUES, filed on Jul. 12, 2007, which is incorporated herein by reference in its entirety.

STATEMENT REGARDING FEDERALLY SPONSORED RESEARCH OR DEVELOPMENT

This invention was made partially with U.S. Government support from the National Institute of Health under NIH Grant R15 GM 069562-01. The U.S. Government has certain rights in the invention.

BACKGROUND

Prior art bioreactors were unable to provide optimal growth of root mass due to limitations caused by the size of the droplets used in the prior art mist systems, the high air flow in the prior art systems, and the fixed size/volume culture chamber. All of these prior art factors prohibited scaling up the mist reactor beyond about 1 L.

SUMMARY

These and other deficiencies in the prior art are addressed by the flexible wall bioreactor described herein that uses a small droplet size, lower gas flow rates, and a flexible culture chamber to offer scalability, to provide a more optimal environment for the growth of dense root beds, shoot cultures, and 2 and 3 dimensional animal tissues, and yet to retain the benefits of the gentle nonshear environment offered by a mist fed system.

BRIEF DESCRIPTION OF THE DRAWINGS

These and other features, aspects, and advantages of the present invention will become better understood with regard to the following description, appended claims, and accompanying drawings. The drawings are not necessarily to scale, emphasis instead being placed on illustration of principles of the invention. The drawings include the following figures:

DETAILED DESCRIPTION OF THE DRAWINGS

The present invention may be understood by the following detailed description, which should be read in conjunction with the attached drawings. The following detailed description of certain embodiments is by way of example only and is not meant to limit the scope of the present invention.

Hairy root is a plant disease caused by *Agrobacterium rhizogenes*, which is a gram-negative soil bacterium. When the bacterium infects the plant, the T-DNA between the TR and TL regions of the Ri plasmid in the bacterium is transferred and integrated into the nuclear genome of the host plant. The transformation process produces a valuable byproduct, hairy root, which will form at or near the site of infection. In addition, opines are produced and serve as a specific food for the bacteria. Hairy roots grow rapidly, show ageotropic growth, and are often highly branched on phytohormone-free medium. The transformed root is highly differentiated and can cause stable and extensive production of secondary metabolites. In addition, *A. rhizogenes* can transfer T-DNA from binary vectors and enable the production of transgenic plants containing foreign genes carried on a second plasmid, which can be used to produce transgenic plants. The optimization of nutrients for hairy root growth is critical to gain a high production of secondary metabolites or transgenic protein products.

Figure 1:
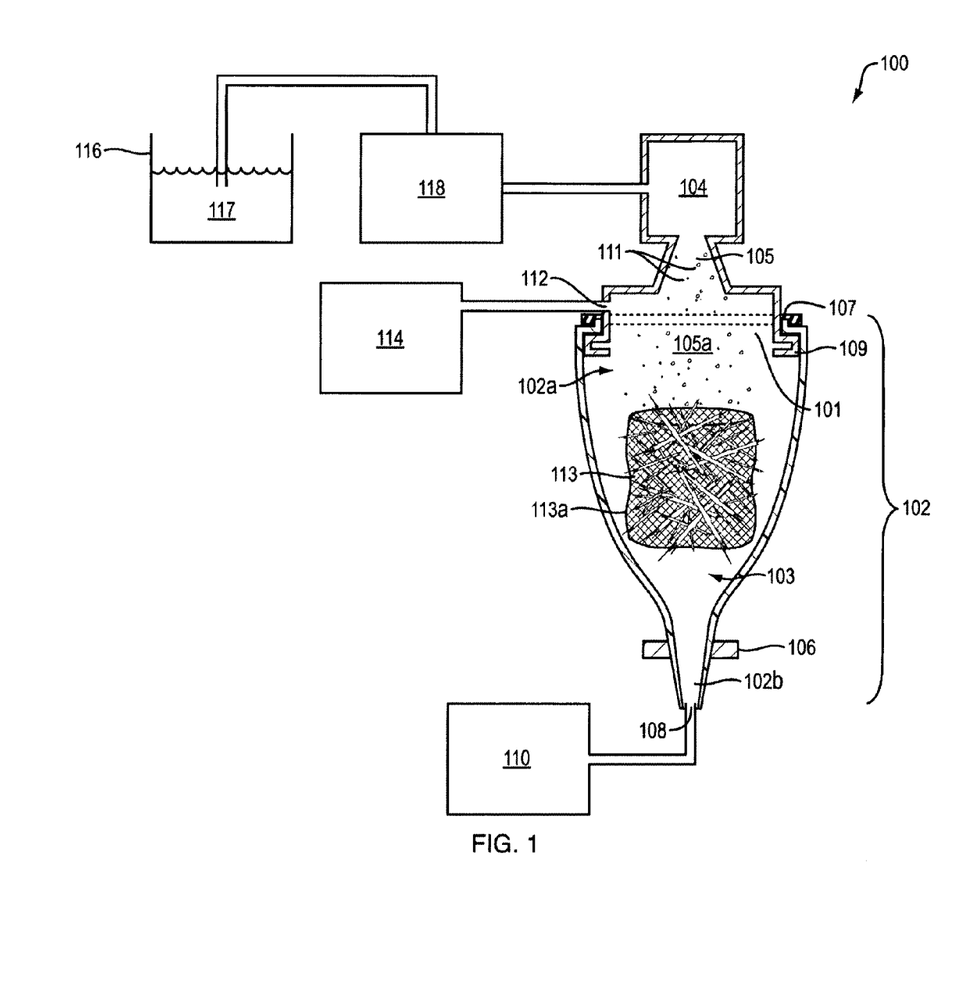
FIG. 1 is a side view of one embodiment of the present invention.

A gas-phase (mist) flexible bioreactor is described below that reduces gas exchange limitations, does not oxygen limit the root growth, and allows the maximum root tissue concentration to develop by delivering oxygen and nutrients to a dense root bed. As depicted in FIG. 1, the flexible bioreactor 100 incorporates a flexible wall growth chamber 102. The flexible wall growth chamber 102 allows for the increase in density of the inoculums root bed 113 that may be disposed directly within the flexible growth chamber 102, or alternatively may be disposed inside a tubular open mesh growth trellis 113a. As the root bed 113 grows, the flexible chamber 102 can expand and maintain a reasonable density of roots within root bed 113. An inlet port 105 is coupled to an upper opening 101 of the flexible growth chamber 102. The upper opening 101 is sealed against the inlet port 105 such that interior of the inlet port 105a and interior 103 of flexible growth chamber 102 are in communication with one another and are isolated from the exterior environment. A liquid growth medium reservoir 116 containing liquid growth medium 117 is fluidly coupled to a pump 118 that has an output of liquid growth medium that is provided to a mister 104. The mister 104 is used to deliver growth medium mist 111 in a desired droplet size range at much higher growth medium flow rates than prior art devices. The output of the mister 104 is fluidly coupled to the inlet port 105 so as to provide the growth medium mist 111 into the interior 103 of the flexible growth chamber 102. The flexible growth chamber 102 is constricted using a constriction band 106 such that the interior 103 of the flexible growth chamber is divided forming an upper chamber 102a and a lower chamber 102b. As the root bed 113 continues to grow, at a certain size the constriction band 106 is removed to allow the root bed 113 to take up all the available volume within flexible growth chamber 102. As growth medium mist 111 is deposited in the interior 103 of the flexible growth chamber 102, the deposited liquid growth medium 117 will flow downward into lower chamber 102b. Growth medium 117 is removed from the lower chamber 102b via a bottom opening 108 connected to a pump 110. A gas inlet vent 112 is connected to a pump 114 to provide ambient air, or other selected gases or gas mixtures to flow into the upper chamber 102a of the flexible growth chamber 102. The gas inlet vent 112 may be through the inlet port 105 or may alternatively be through the wall of the flexible growth chamber 102. The pump 118 may be a peristaltic pump having a pulse dampener.

The mister 104, which can be a Sono Tek ultrasonic mister is capable of providing a volumetric throughput of 4 L min$^{-1}$ and of providing droplets having a diameter of approximately 18 μm. This droplet size, which may vary between 5 μm and 25 μm, avoids the problems of the prior art in which larger droplets diameters (typically exceeding 50 μm) resulted in water logging of the root bed causing gas exchange within the root bed to drop. The size of the droplets provided by mister 104 should offer good aeration and control of the gas phase composition, reduces shear damage to the root bed 113, and also reduce any chemical gradients within the flexible growth chamber 102 during growth of the root bed 113. The use of a small droplet size allows the use of the mist deposition model in which root beds are treated as if they are fibrous filters. It should be noted that as the present embodiment is scaled up in size, other flow rates and duty cycles may be selected. However, it is know that providing for continuous misting is injurious to tissue growth.

In the mist deposition model, for a fixed droplet size $D_p$, the droplet capture efficiency ($\eta_B$) of the root bed is given by $\eta_B = 1 - \exp[(-4 L \alpha \eta_C)/(D_R(1-\alpha))]$ where L is the length of the root bed, $D_R$ is the diameter of the root, and $\eta_C$ is the combined capture efficiency due to impaction and interception ($\eta_{(IMP+INT)}$), and diffusion ($\eta_D$), and these efficiencies are all functions of $D_p$.

The overall mass deposition efficiency ($\eta_{OM}$) of the root bed is the product of the root bed efficiency $\eta_B(D_{pi})$ and the mass fraction $m(D_{pi})$ of mist particles of diameter $D_{pi}$, summed over the aerosol size distribution data: $\eta_{OM} = \Sigma_i \eta_B(D_{pi}) \times m(D_{pi})$. The medium captured by the roots ($V_{dep}$, mL d$^{-1}$) is expressed as $V_{dep} = 24 \, \omega \times Q_L \times \eta_{OM}$, where the factor 24 converts from hours to days, ω is the duty cycle (min hr$^{-1}$) of the mist, and $Q_L$ is the medium flow rate (mL min$^{-1}$) during the mist "on" cycle. $V_{dep}$ is therefore a non-linear function of α (packing fraction of root bed).

The medium required to support the growth of the root bed ($V_{req}$, mL d$^{-1}$) depends upon the amount of biomass present, the growth rate $\mu(d^{-1})$, the apparent biomass yield of the growth-limiting nutrient $Y_{x/s}$ (g DW biomass per g nutrient consumed) and the concentration of the limiting nutrient medium $C_S$ (g L$^{-1}$). To maintain a desired growth rate μ, $V_{dep}$ must be greater than or equal to $V_{req}$.

Figure 2:
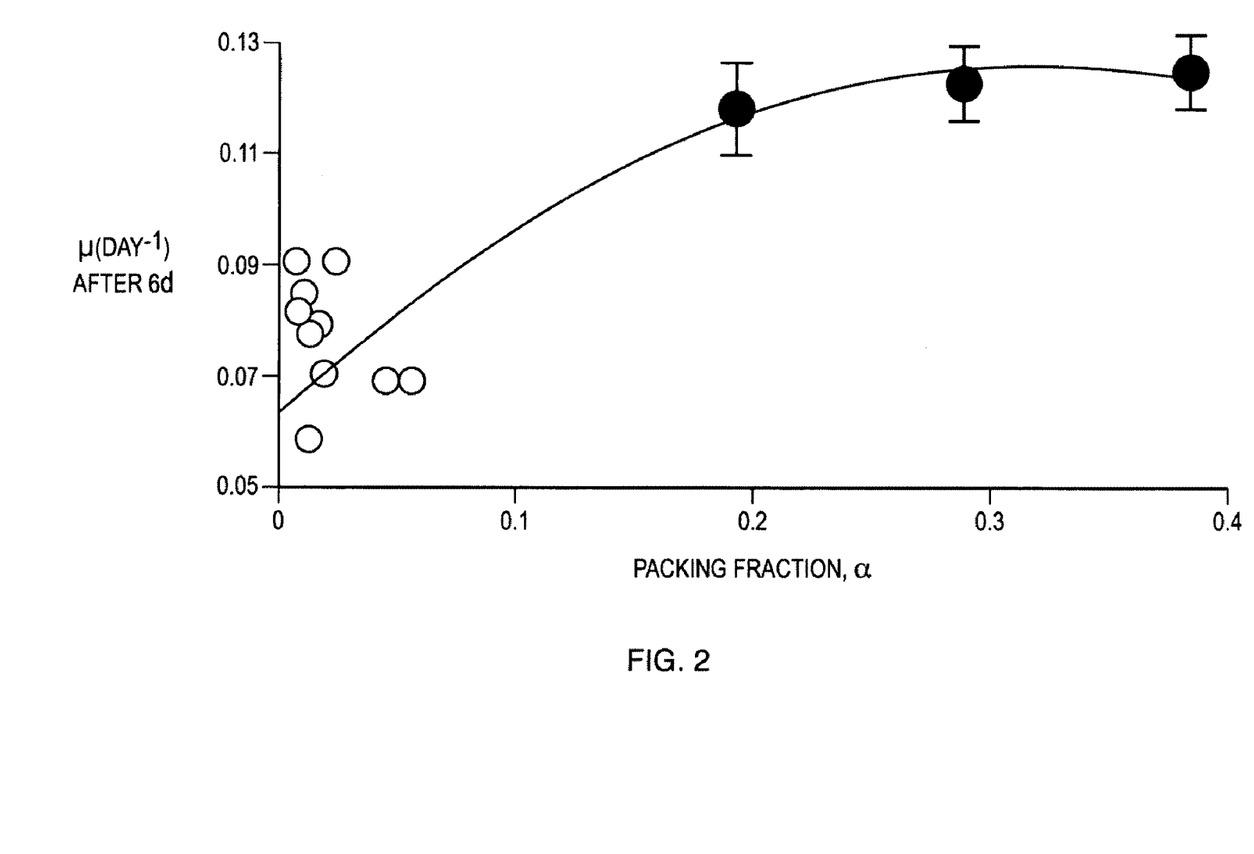
FIG. 2 is a graph of growth rate, $\mu$, vs. packing factor, $\alpha$.

FIG. 2 depicts the relationship between packing fraction α and the growth rate μ. $V_{dep}$ is a strong non-linear function of α and as can be seen in FIG. 2, where increasing α supports a higher growth rate by allowing more nutrients to be captured by the roots. Thus, densely packed root beds grow better in the flexible bioreactor 100 described herein and therefore cost effective operation of the flexible bioreactor 100 described herein begins with low inoculum levels that grow into high yields.

Figure 3A:
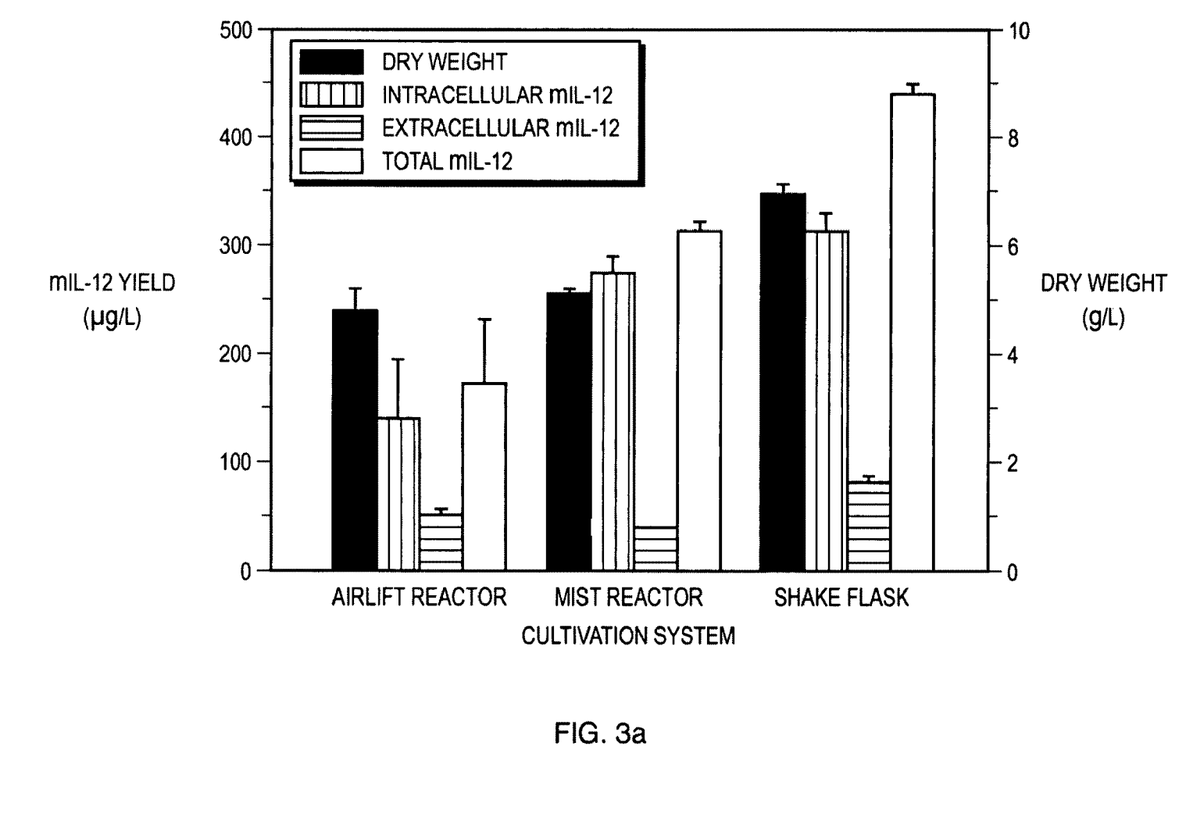
FIG. 3a is a graph of dry weight and yield of various growth systems.
Figure 3B:
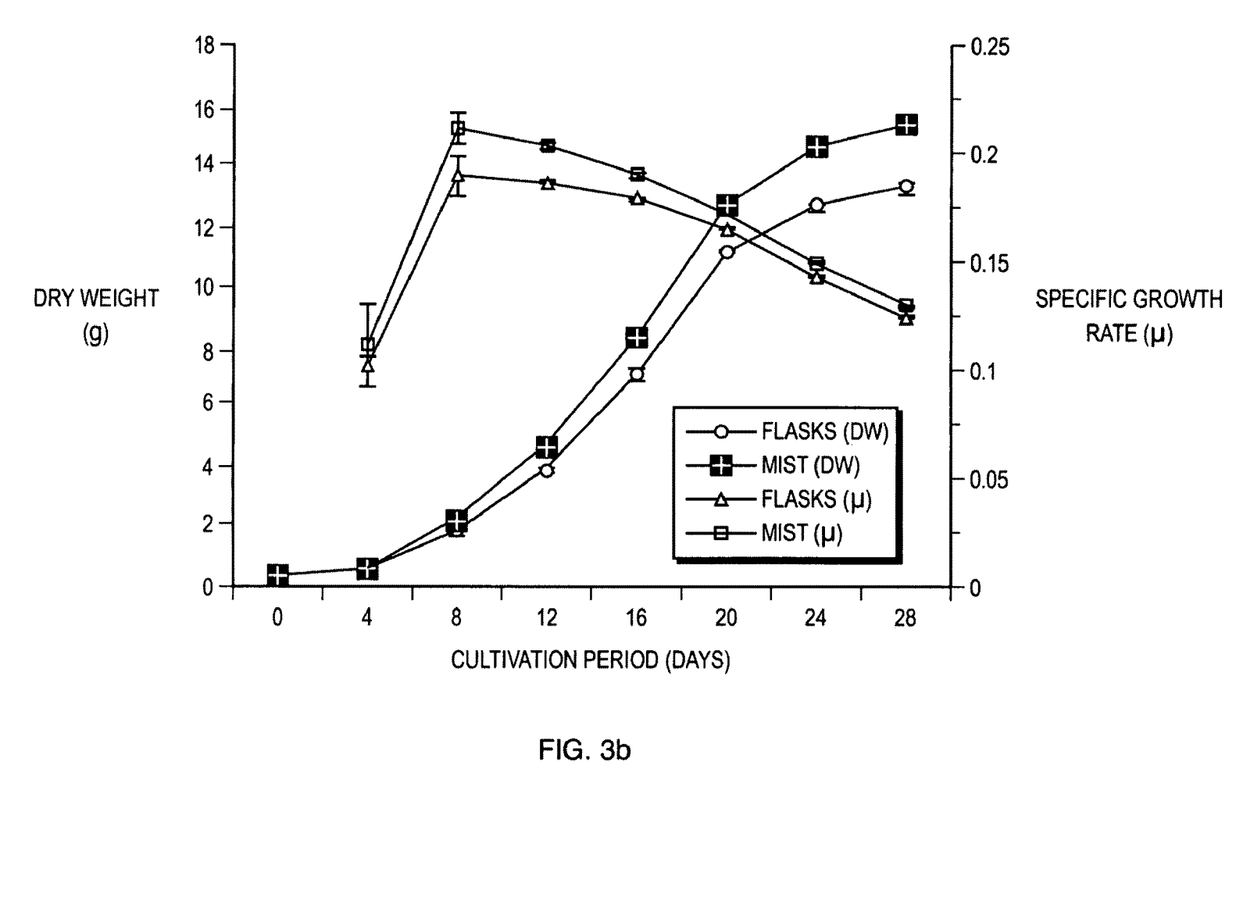
FIG. 3b is a graph of dry weight and specific growth rate over time.

FIGS. 3a and 3b depict an example of the dry weight and yield of an airlift reactor, mist reactor and shake flask. It is noted that the results from a shake flask are typically a first bench mark used to compare the growth rate of other methodologies, e.g., the flexible bioreactor 100 described herein.

Figure 4:
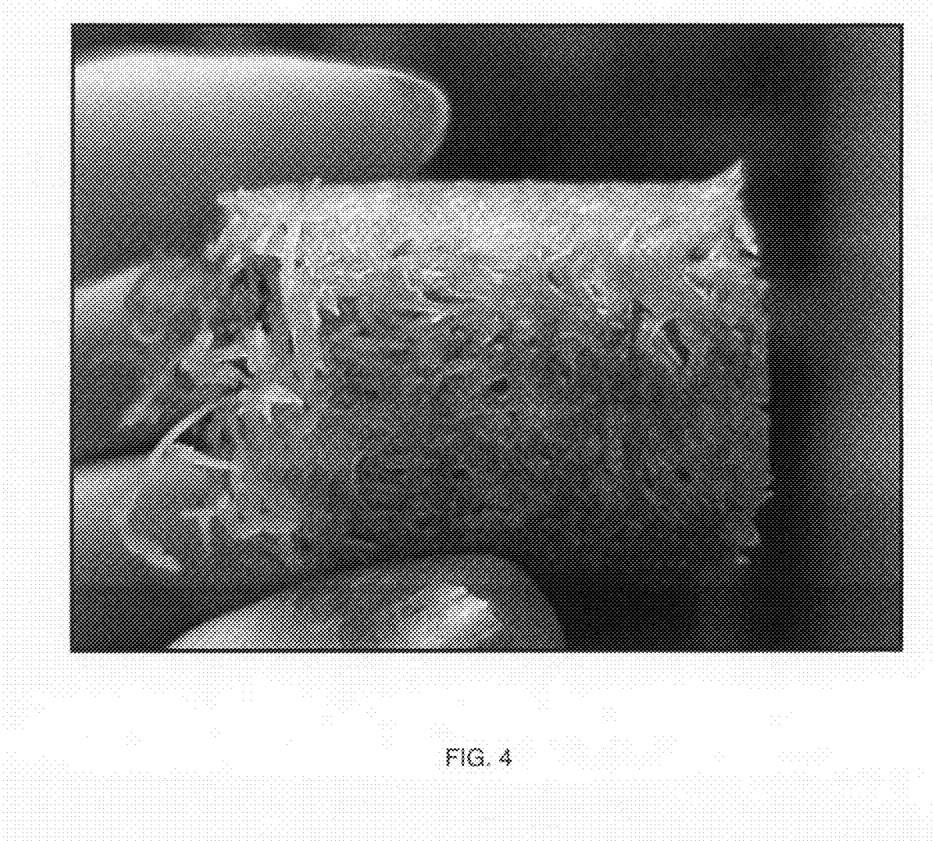
FIG. 4 is a picture of a dense root bed approximately 2.7 cm in diameter.

FIG. 4 depicts an example of high density root bed produced by the bioreactor described herein in which the roots appear healthy and non-necrotic throughout the dense root bed.

Carbon is the predominate source of energy for hairy roots. Therefore, increasing the total carbon, either by increasing the carbon concentration of the growth medium, typically by increasing the sugar concentration ($C_s$), or by increasing the duty cycle ω should also increase the growth rate. The volume of medium, $V_{req}$, required by the roots to grow at a particular growth rate, μ, is inversely proportional to the nutrient concentration $C_s$. Increasing $C_s$ should therefore decrease $V_{req}$ for a fixed growth rate, μ, or increase growth rate, μ, at fixed $V_{dep}$.

Figure 5A:
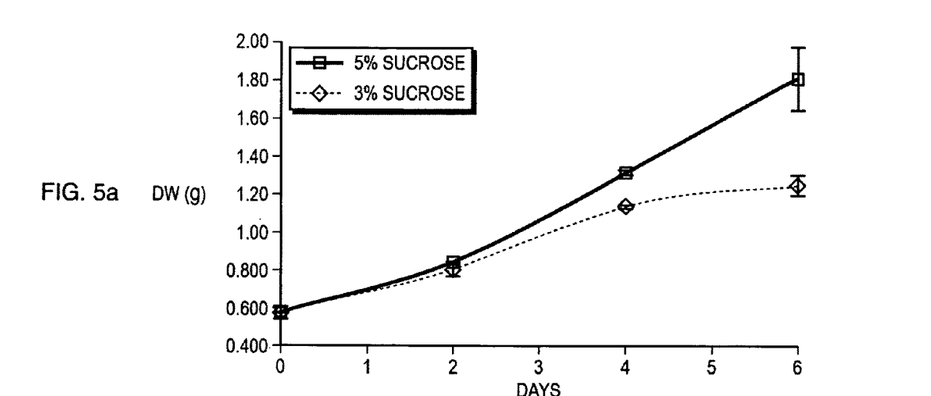
FIGS. 5a-5c are graphs depicting DW, growth rate, $\mu$, and DW/FW for varied medium concentrations.
Figure 5B:
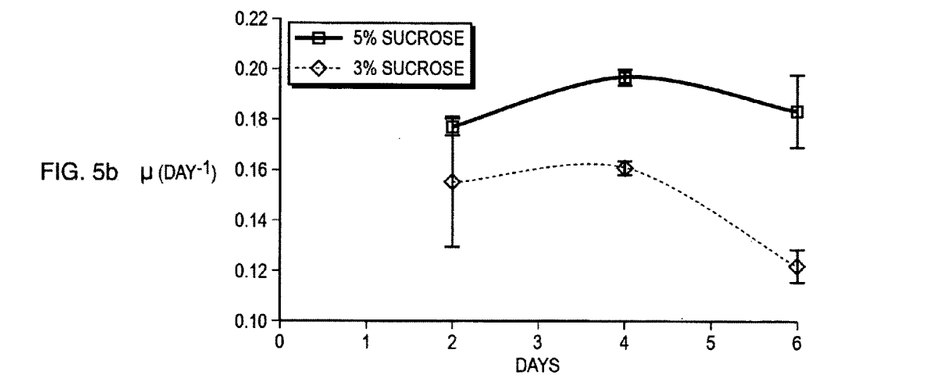
Figure 5C:
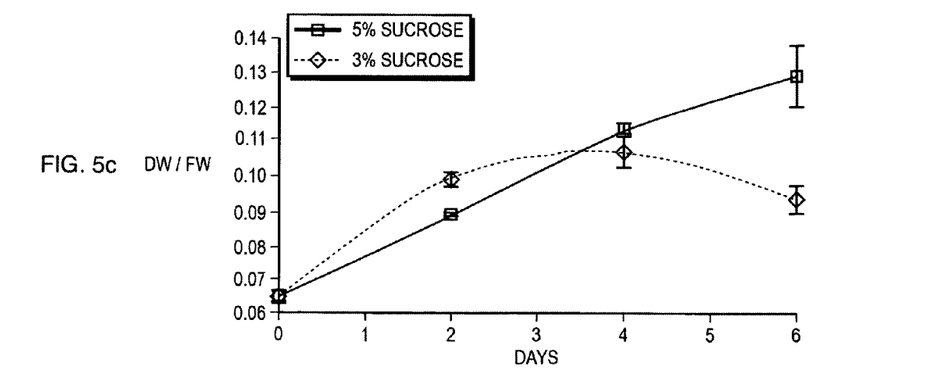
Figure 6A:
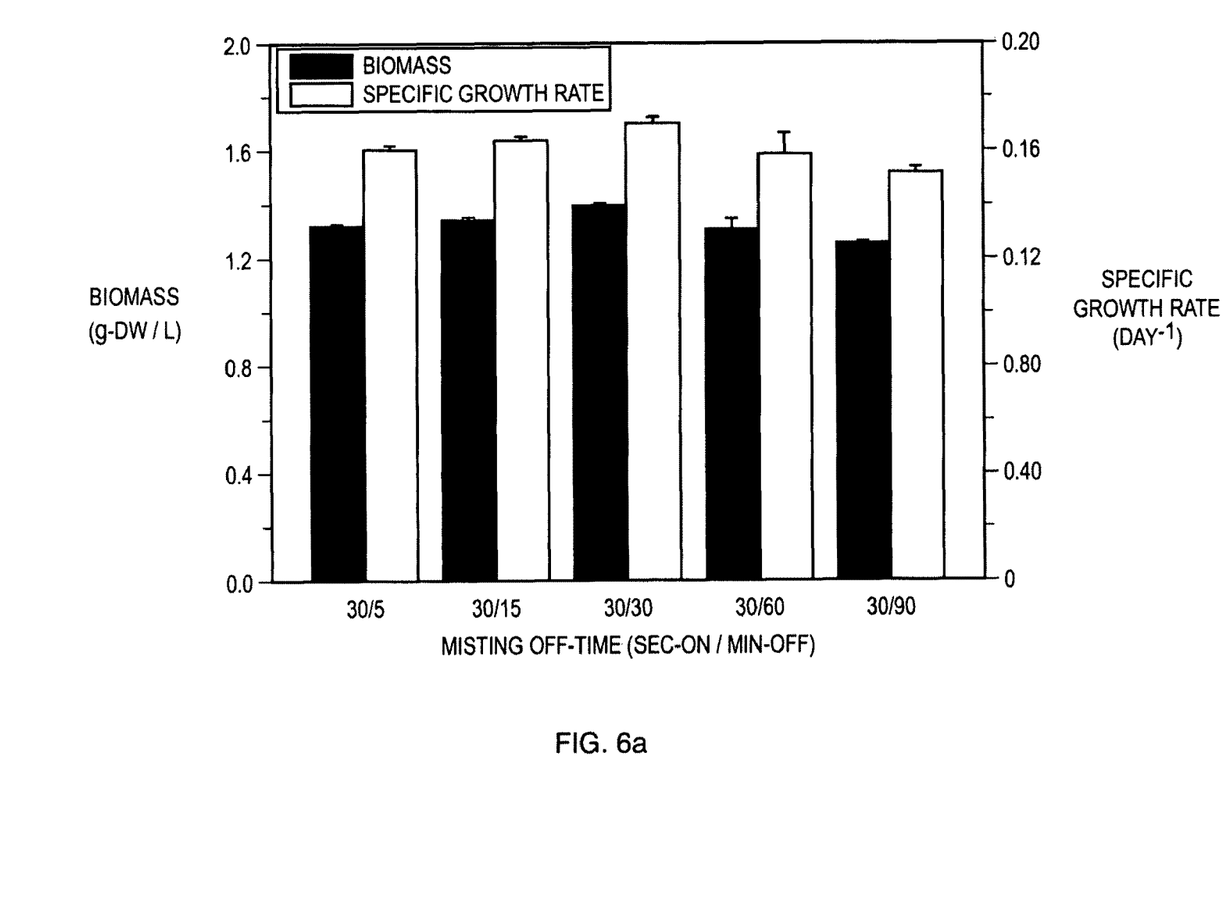
FIGS. 6a and 6b are graphs depicting growth rate, $\mu$, v. mist duty-cycle time.
Figure 6B:
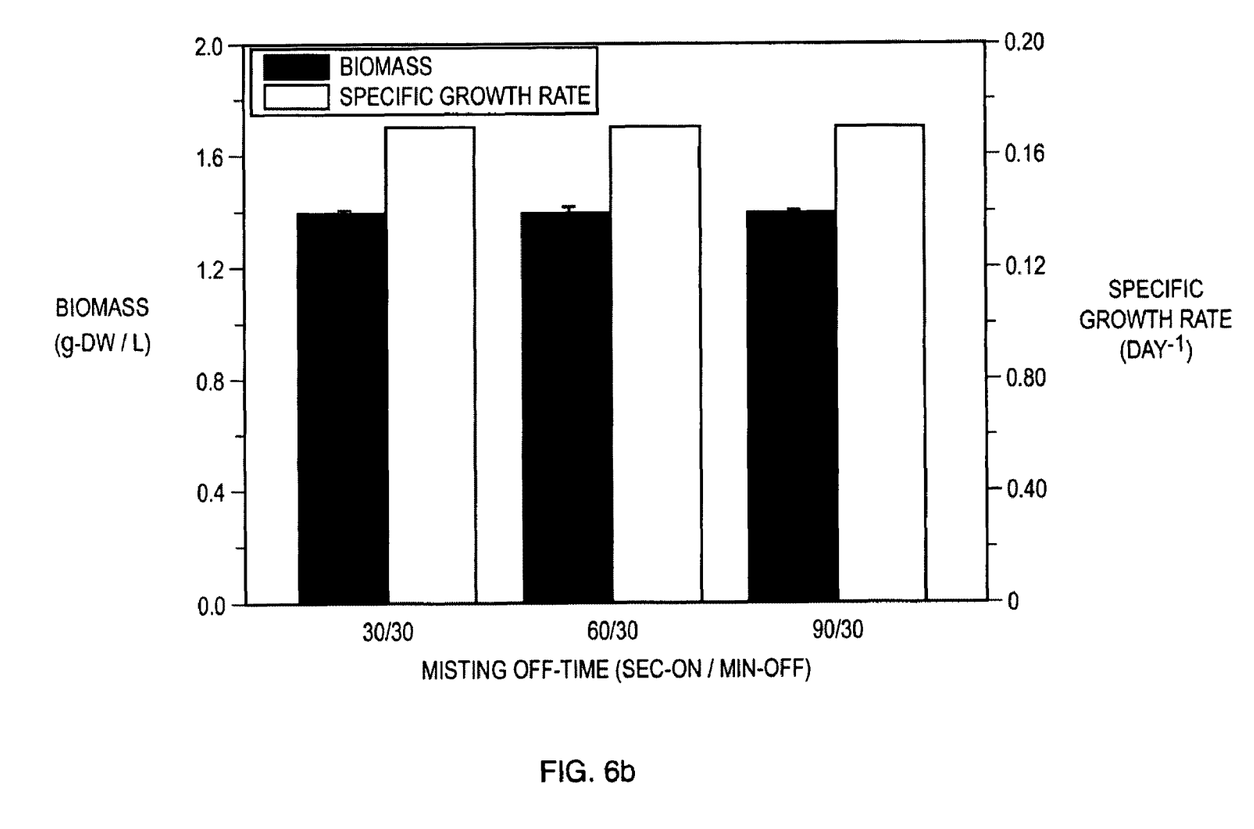

FIGS. 5a-5c depict the results for varying the concentration of sucrose in the growth medium. As depicted in FIG. 5a, roots grown in a 5% concentration of sucrose showed significantly more biomass than roots grown in a 3% concentration. As depicted in FIG. 5b, although the highest rate of growth occurred at day 4 for both sugar levels, carbon as measured by total sugar was not depleted in this time period. As depicted in FIG. 5c the DW/FW ratio continued to increase in the 5% sucrose medium. FIGS. 6a and 6b depict the results of varying the mist duty cycle, ω. These results were obtained using a sugar concentration that was provided at inoculation.

In the bioreactor depicted in FIG. 1, the mist delivery system is substantially independent of the gas delivery so that vvm rates can be significantly lower than the prior art. This avoids the problems in the prior art of having high gas delivery that inhibited growth by stripping beneficial gases from the root bed, such as $CO_2$. The gas flow rate will in general be a function of the growth rate, μ, the size of the bioreactor chamber, and the type of inoculum used.

One issue involved in the use of the flexible bioreactor described herein is that in vitro plant cultures are easily contaminated with bacteria and fungi because of the long growth period in the sugar rich medium. To avoid this problem, the mister 104 is cold sterilized as follows. The mister 104 is soaked overnight in 70% ethanol followed by pumping (25 mL min$^{-1}$) 500 mL of a solution of 10% bleach, then 100 mL sterile water, 500 mL of a solution of 70% ethanol, and finally a solution of 100 mL sterile water. Growth medium, typically B5 medium+5% (w/v) sucrose+0.1% (v/v) PPM is filter sterilized and added to the medium reservoir. An alternative sterilization method involves the following. Briefly, the mister head is washed with tap water to remove any large debris, dried at 60° C., wrapped in aluminum foil, and heated again at 60° C. for 12 hours. Following this heating step, the mister head is heated again at 115° C. for 2 hours. Before being inserted into the mist bioreactor, the misting head is cooled in a laminar flow hood. A third sterilization procedure may involve gas-phase sterilization using ethylene oxide. Inoculum roots are placed in the upper chamber 102a just above the constriction band 106. The constriction band can be located at various points along the bag depending upon the type of material being cultured. As example, to fill a bag to its maximum with roots, the inoculum is placed on a constriction located about 75% down the height of the bag. For shoot cultures, on the other hand, inoculum is seated in the bag at a constriction located closer to the bottom of the bag.

In one embodiment, the upper chamber 102a is sized and dimensioned such that the headspace distance between the mister 104 and the root bed must be 20 cm to ensure uniform medium distribution. This distance is a function of the spray diameter provided by one placement location of the mister 104 and is selected to provide the maximum penetration depth of the droplets into the root bed. With scale-up, however, the diameter of the bag may be increased to 50 cm if the mister head is seated lower through the cap thereby producing a broader spray angle.

The flexible wall growth chamber 102 may be constructed of transparent 3 mil thick polypropylene sheeting with necked portions for the insertion and exit ports for liquid and gas. The side seams are sealed and the large inlet port 105 is inserted into the bag. The inlet port 105 may be plastic and have a shoulder region wherein the polypropylene bag is then held in place by a silicone rubber O-ring 107 above the shoulder region. The bottom seam is then sealed and the liquid and gas ports are inserted and sealed into the bag. The misting unit 104 is inserted into the inlet port 105 and sealed using silicone sealer or glue.

In general, the rate at which the nutrients flow into the flexible chamber and the concentration of the nutrient solution itself, are a function of the biomass and biological species used in the flexible chamber as well as the tissue, e.g., root or plant, morphology. In addition, the flow rate and concentration will also change as the system is scaled into larger versions. For example, multiple misters may be used resulting in lower flow rates per mister, but a larger overall flow rate. Thus, these various flow rates may be provided for by adjusting the duty cycle of the mister in addition to adjusting the flow rate through the mister itself. Duty cycles may range from 30 seconds on and 5 minutes off to 15 minutes on and 90 minutes off. In addition, various gases may be mixed together and provided via pump 114. This may include ambient air mixed with carbon dioxide or other selected gases.

Although the present flexible bioreactor has been described as being used to produce dense root beds the flexible bioreactor described herein could also could be used to produce shoot cultures as well. In this embodiment, the nutrient flow rate, gas flow rate, and gas mixture would have to be adjusted for the particular species, biomass, and leaf and root morphologies.

While the present invention has been particularly shown and described with references to preferred embodiments thereof it will be understood by those skilled in the art that various changes in form and details may be made therein without departing from the spirit and scope of the invention as defined by the appended claims. All the features disclosed in this specification, including any accompanying claims, abstract, and drawings, may be replaced by alternative features serving the same, equivalent or similar purpose, unless expressly stated otherwise.

The invention claimed is:

1. A gas phase bioreactor comprising:
   a gas pump having an output of pumped gas;
   a growth medium reservoir containing liquid growth medium;
   a growth medium pump fluidly coupled to said liquid growth medium and operative to provide an output pumped liquid growth medium;
   a mister coupled to said output of growth medium pump and having an output operative to provide an output of growth medium mist having a droplet size;
   an inlet port having an interior and an exterior, said inlet port interior fluidly coupled to said output of said mister;
   a flexible growth chamber having an interior, an exterior, a top opening, and a bottom opening, said top opening being coupled to said inlet port such that said flexible growth chamber interior is communicably coupled to said inlet port interior, said flexible growth chamber interior is further communicably coupled to said output of said gas pump, wherein said pumped gas and said growth medium mist are provided within the flexible growth chamber interior, said flexible growth chamber top opening being coupled to said inlet port so as to prevent leakage of said air and said growth medium mist to the exterior of said flexible growth chamber;

said growth medium reservoir being located on said exterior of said flexible growth chamber;

an adjustable constriction member placed on the exterior of said flexible growth chamber between said top and bottom openings and operative to separate said flexible growth chamber interior into first and second chambers, wherein said second chamber includes said bottom opening; and wherein said growth medium mist deposited in said flexible chamber interior is capable of flowing downward into said second chamber and through said bottom opening which permits removal of the growth medium mist that has flowed into said second chamber.

2. The gas phase bioreactor of claim 1 wherein said inlet port includes a shoulder portion and wherein said flexible growth chamber is coupled to said inlet port via a resilient member on the exterior of said inlet port above said shoulder region.

3. The gas phase bioreactor of claim 1 wherein said droplet size has a diameter between 5 μm and 25 μm.

4. The gas phase bioreactor of claim 3 wherein said droplet size has a diameter substantially 18 μm.

5. The gas phase bioreactor of claim 1 wherein said liquid growth medium pump is capable of providing between 25 mL/min and 4 L/min.

6. The gas phase bioreactor of claim 1 wherein the liquid growth medium includes a sugar concentration of between 2% and 6% concentration.

7. The gas phase bioreactor of claim 6 wherein the liquid growth medium includes a sugar concentration of substantially 5% concentration.

8. The gas phase bioreactor of claim 1 wherein said mister includes a pulsed output having a duty cycle.

9. The gas phase bioreactor of claim 1 wherein said duty cycle is between a low duty cycle that is on for 30 seconds on and off for 5 minutes off and an upper duty cycle that is on for 15 minutes and off for 90 minutes.

10. The gas phase bioreactor of claim 1 wherein said gas pump output and said mister output are independent of one another.

11. The gas phase bioreactor of claim 1 further including a root bed within said first chamber of said flexible growth chamber.

12. The gas phase bioreactor of claim 11 wherein said first chamber is sized and dimensioned such that the distance between the output of said mister and said root bed is substantially 20 cm.

13. The gas phase bioreactor of claim 1 wherein said gas includes ambient air.

14. The gas phase bioreactor of claim 13 wherein said gas further includes other gases.

15. The gas phase bioreactor of claim 14 wherein said other gas includes ethylene.

16. The gas phase bioreactor of claim 14 wherein said other gas includes carbon dioxide.

17. The gas phase bioreactor of claim 1 further including shoot cultures within said first chamber of said flexible growth chamber.

* * * * *